(12) United States Patent
Nunn et al.

(10) Patent No.: US 9,370,457 B2
(45) Date of Patent: Jun. 21, 2016

(54) INFLATABLE AIR MATTRESS SNORING DETECTION AND RESPONSE

(71) Applicants: Select Comfort Corporation, Minneapolis, MN (US); BAM Labs, Inc., Campbell, CA (US)

(72) Inventors: Rob Nunn, Eden Prairie, MN (US); Wade Daniel Palashewski, Andover, MN (US); Matthew Wayne Tilstra, Rogers, MN (US); Stacy Stusynski, Blaine, MN (US); Steven Young, Campbell, CA (US); Carl Hewitt, Campbell, CA (US)

(73) Assignees: Select Comfort Corporation, Minneapolis, MN (US); Bam Labs, INC., Campbell, CA (US)

( * ) Notice: Subject to any disclaimer, the term of this patent is extended or adjusted under 35 U.S.C. 154(b) by 2 days.

(21) Appl. No.: 14/206,841

(22) Filed: Mar. 12, 2014

(65) Prior Publication Data

US 2014/0259417 A1    Sep. 18, 2014

Related U.S. Application Data

(60) Provisional application No. 61/782,394, filed on Mar. 14, 2013.

(51) Int. Cl.
*A47C 31/00* (2006.01)
*A61G 7/015* (2006.01)
(Continued)

(52) U.S. Cl.
CPC ............. *A61G 7/015* (2013.01); *A47C 27/083* (2013.01); *A47C 31/00* (2013.01); *A61B 5/4818* (2013.01); *A61B 5/6892* (2013.01)

(58) Field of Classification Search
CPC ..... A61G 7/015; A61G 7/018; A61B 5/6892; A61B 5/4818; A47C 31/00; A47C 27/083
USPC .............................................. 5/614, 615, 617
See application file for complete search history.

(56) References Cited

U.S. PATENT DOCUMENTS

| 3,727,606 A | 4/1973 | Sielaff |
| 3,998,209 A | 12/1976 | Macvaugh |
| 4,146,885 A | 3/1979 | Lawson, Jr. |

(Continued)

FOREIGN PATENT DOCUMENTS

| DE | 40 05 822 | 8/1991 |
| GB | 2 471 401 | 12/2010 |

(Continued)

OTHER PUBLICATIONS

U.S. Appl. No. 13/933,285, filed Jul. 2, 2013, Palashewski.

(Continued)

*Primary Examiner* — Robert G Santos
*Assistant Examiner* — Myles Throop
(74) *Attorney, Agent, or Firm* — Fish & Richardson P.C.

(57) ABSTRACT

A method can be provided that includes measuring sound waves using a sound measuring device, determining, at a central controller of an air mattress system, one or more parameter values of the sound waves, comparing the one or more parameter values with values, ranges, or patterns indicative of snoring, identifying a snoring state of a user, and initiating, with the central controller, a change to one or more adjustable features of the air mattress system.

11 Claims, 8 Drawing Sheets

(51) Int. Cl.
   *A47C 27/08*   (2006.01)
   *A61B 5/00*   (2006.01)

(56) References Cited

U.S. PATENT DOCUMENTS

| | | | |
|---|---|---|---|
| 4,299,233 A | 11/1981 | Lemelson | |
| 4,657,026 A | 4/1987 | Tagg | |
| 4,662,012 A | 5/1987 | Torbet | |
| 4,766,628 A | 8/1988 | Walker | |
| 4,788,729 A | 12/1988 | Walker | |
| 4,829,616 A | 5/1989 | Walker | |
| 4,890,344 A | 1/1990 | Walker | |
| 4,897,890 A | 2/1990 | Walker | |
| 4,908,895 A | 3/1990 | Walker | |
| 4,991,244 A | 2/1991 | Walker | |
| 5,062,169 A | 11/1991 | Kennedy et al. | |
| 5,144,706 A | 9/1992 | Walker | |
| 5,170,522 A | 12/1992 | Walker | |
| 5,197,490 A | 3/1993 | Steiner et al. | |
| 5,459,452 A | 10/1995 | DePonte | |
| 5,509,154 A | 4/1996 | Shafer et al. | |
| 5,515,865 A | 5/1996 | Scanlon | |
| 5,564,140 A | 10/1996 | Shoenhair et al. | |
| 5,642,546 A | 7/1997 | Shoenhair | |
| 5,652,484 A | 7/1997 | Shafer et al. | |
| 5,675,855 A | 10/1997 | Culp | |
| 5,684,460 A | 11/1997 | Scanlon | |
| 5,699,038 A | 12/1997 | Ulrich et al. | |
| 5,724,990 A | 3/1998 | Ogino | |
| 5,765,246 A | 6/1998 | Shoenhair | |
| 5,771,511 A | 6/1998 | Kummer et al. | |
| 5,796,340 A | 8/1998 | Miller | |
| 5,844,488 A | 12/1998 | Musick | |
| 5,848,450 A | 12/1998 | Oexman et al. | |
| 5,903,941 A | 5/1999 | Shafer et al. | |
| 5,904,172 A | 5/1999 | Gifft et al. | |
| 5,948,303 A | 9/1999 | Larson | |
| 5,964,720 A | 10/1999 | Pelz | |
| 5,989,193 A | 11/1999 | Sullivan | |
| 6,024,699 A | 2/2000 | Surwit et al. | |
| 6,037,723 A | 3/2000 | Shafer et al. | |
| 6,058,537 A | 5/2000 | Larson | |
| 6,062,216 A | 5/2000 | Corn | |
| 6,079,065 A | 6/2000 | Luff et al. | |
| 6,108,844 A | 8/2000 | Kraft et al. | |
| 6,120,441 A | 9/2000 | Griebel | |
| 6,146,332 A | 11/2000 | Pinsonneault et al. | |
| 6,147,592 A | 11/2000 | Ulrich et al. | |
| 6,161,231 A | 12/2000 | Kraft et al. | |
| 6,202,239 B1 | 3/2001 | Ward et al. | |
| 6,208,250 B1 | 3/2001 | Dixon et al. | |
| 6,234,642 B1 | 5/2001 | Bokamper | |
| 6,272,378 B1 | 8/2001 | Baumgart-Schmitt | |
| 6,386,201 B1 * | 5/2002 | Fard | 128/848 |
| 6,396,224 B1 | 5/2002 | Luff et al. | |
| 6,397,419 B1 | 6/2002 | Mechache | |
| 6,438,776 B2 | 8/2002 | Ferrand et al. | |
| 6,450,957 B1 | 9/2002 | Yoshimi et al. | |
| 6,468,234 B1 | 10/2002 | Ford et al. | |
| 6,483,264 B1 | 11/2002 | Shafer et al. | |
| 6,485,441 B2 | 11/2002 | Woodward | |
| 6,546,580 B2 | 4/2003 | Shimada | |
| 6,547,743 B2 | 4/2003 | Brydon | |
| 6,561,047 B1 | 5/2003 | Gladney | |
| 6,566,833 B2 | 5/2003 | Bartlett | |
| 6,643,875 B2 | 11/2003 | Boso et al. | |
| 6,686,711 B2 | 2/2004 | Rose et al. | |
| 6,698,432 B2 | 3/2004 | Ek | |
| 6,708,357 B2 | 3/2004 | Gaboury et al. | |
| 6,719,708 B1 | 4/2004 | Jansen | |
| 6,763,541 B2 | 7/2004 | Mahoney et al. | |
| 6,778,090 B2 | 8/2004 | Newham | |
| 6,804,848 B1 | 10/2004 | Rose | |
| 6,832,397 B2 | 12/2004 | Gaboury et al. | |
| 6,840,117 B2 | 1/2005 | Hubbard, Jr. | |
| 6,840,907 B1 | 1/2005 | Brydon | |
| 6,847,301 B1 | 1/2005 | Olson | |
| 6,878,121 B2 | 4/2005 | Krausman | |
| 6,883,191 B2 | 4/2005 | Gaboury et al. | |
| 6,993,380 B1 | 1/2006 | Modarres | |
| 7,041,049 B1 | 5/2006 | Raniere | |
| 7,077,810 B2 | 7/2006 | Lange et al. | |
| 7,150,718 B2 | 12/2006 | Okada | |
| 7,237,287 B2 | 7/2007 | Weismiller et al. | |
| 7,253,366 B2 | 8/2007 | Bhai | |
| 7,304,580 B2 | 12/2007 | Sullivan et al. | |
| 7,314,451 B2 | 1/2008 | Halperin et al. | |
| 7,321,811 B1 | 1/2008 | Rawls-Meehan et al. | |
| 7,330,127 B2 | 2/2008 | Price et al. | |
| 7,389,554 B1 | 6/2008 | Rose | |
| 7,396,331 B2 | 7/2008 | Mack | |
| 7,429,247 B2 | 9/2008 | Okada et al. | |
| 7,437,787 B2 | 10/2008 | Bhai | |
| 7,465,280 B2 | 12/2008 | Rawls-Meehan | |
| 7,480,951 B2 | 1/2009 | Weismiller | |
| 7,506,390 B2 | 3/2009 | Dixon et al. | |
| 7,520,006 B2 | 4/2009 | Menkedick et al. | |
| 7,524,279 B2 | 4/2009 | Auphan | |
| 7,532,934 B2 | 5/2009 | Lee et al. | |
| 7,538,659 B2 | 5/2009 | Ulrich et al. | |
| 7,568,246 B2 | 8/2009 | Weismiller et al. | |
| 7,631,377 B1 | 12/2009 | Sanford | |
| 7,637,859 B2 | 12/2009 | Lindback et al. | |
| 7,652,581 B2 | 1/2010 | Gentry et al. | |
| 7,666,151 B2 | 2/2010 | Sullivan et al. | |
| 7,669,263 B2 | 3/2010 | Menkedick et al. | |
| 7,676,872 B2 | 3/2010 | Block et al. | |
| 7,685,663 B2 | 3/2010 | Rawls-Meehan | |
| 7,698,761 B2 | 4/2010 | Neuenswander et al. | |
| 7,699,784 B2 | 4/2010 | Wan et al. | |
| 7,717,848 B2 | 5/2010 | Heruth et al. | |
| 7,749,154 B2 | 7/2010 | Cornel | |
| 7,784,128 B2 | 8/2010 | Kramer | |
| 7,785,257 B2 | 8/2010 | Mack et al. | |
| 7,805,785 B2 | 10/2010 | Rawls-Meehan | |
| 7,841,031 B2 | 11/2010 | Rawls-Meehan | |
| 7,849,545 B2 | 12/2010 | Flocard et al. | |
| 7,854,031 B2 | 12/2010 | Rawls-Meehan | |
| 7,860,723 B2 | 12/2010 | Rawls-Meehan | |
| 7,862,523 B2 | 1/2011 | Ruotoistenmaki | |
| 7,865,988 B2 | 1/2011 | Koughan et al. | |
| 7,868,757 B2 | 1/2011 | Radivojevic et al. | |
| 7,869,903 B2 | 1/2011 | Turner et al. | |
| 7,930,783 B2 | 4/2011 | Rawls-Meehan | |
| 7,933,669 B2 | 4/2011 | Rawls-Meehan | |
| 7,953,613 B2 | 5/2011 | Gizewski | |
| 7,954,189 B2 | 6/2011 | Rawls-Meehan | |
| 7,956,755 B2 | 6/2011 | Lee et al. | |
| 7,967,739 B2 | 6/2011 | Auphan | |
| 7,979,169 B2 | 7/2011 | Rawls-Meehan | |
| 8,019,486 B2 | 9/2011 | Rawls-Meehan | |
| 8,020,230 B2 | 9/2011 | Rawls-Meehan | |
| 8,028,363 B2 | 10/2011 | Rawls-Meehan | |
| 8,032,263 B2 | 10/2011 | Rawls-Meehan | |
| 8,032,960 B2 | 10/2011 | Rawls-Meehan | |
| 8,046,114 B2 | 10/2011 | Rawls-Meehan | |
| 8,046,115 B2 | 10/2011 | Rawls-Meehan | |
| 8,046,116 B2 | 10/2011 | Rawls-Meehan | |
| 8,046,117 B2 | 10/2011 | Rawls-Meehan | |
| 8,050,805 B2 | 11/2011 | Rawls-Meehan | |
| 8,052,612 B2 | 11/2011 | Tang | |
| 8,065,764 B2 | 11/2011 | Kramer | |
| 8,069,852 B2 | 12/2011 | Burton | |
| 8,073,535 B2 | 12/2011 | Jung et al. | |
| 8,078,269 B2 | 12/2011 | Suzuki et al. | |
| 8,078,336 B2 | 12/2011 | Rawls-Meehan | |
| 8,078,337 B2 | 12/2011 | Rawls-Meehan | |
| 8,083,682 B2 | 12/2011 | Dalal et al. | |
| 8,090,478 B2 | 1/2012 | Skinner et al. | |
| 8,092,399 B2 | 1/2012 | Sasaki | |
| 8,094,013 B1 | 1/2012 | Lee | |
| 8,096,960 B2 | 1/2012 | Loree, IV et al. | |
| 8,146,191 B2 | 4/2012 | Bobey et al. | |
| 8,150,562 B2 | 4/2012 | Rawls-Meehan | |

(56) References Cited

U.S. PATENT DOCUMENTS

| | | |
|---|---|---|
| 8,166,589 B2 | 5/2012 | Hijlkema |
| 8,181,296 B2 | 5/2012 | Rawls-Meehan |
| 8,266,742 B2 | 9/2012 | Andrienko |
| 8,272,892 B2 | 9/2012 | McNeely et al. |
| 8,276,585 B2 | 10/2012 | Buckley |
| 8,279,057 B2 | 10/2012 | Hirose |
| 8,280,748 B2 | 10/2012 | Allen |
| 8,281,433 B2 | 10/2012 | Riley et al. |
| 8,282,452 B2 | 10/2012 | Grigsby et al. |
| 8,284,047 B2 | 10/2012 | Collins, Jr. et al. |
| 8,287,452 B2 | 10/2012 | Young et al. |
| 8,336,369 B2 | 12/2012 | Mahoney |
| 8,341,784 B2 | 1/2013 | Scott et al. |
| 8,341,786 B2 | 1/2013 | Oexman et al. |
| 8,348,840 B2 | 1/2013 | Heit et al. |
| 8,350,709 B2 | 1/2013 | Receveur |
| 8,375,488 B2 | 2/2013 | Rawls-Meehan |
| 8,376,954 B2 | 2/2013 | Lange et al. |
| 8,382,484 B2 | 2/2013 | Wetmore et al. |
| 8,386,008 B2 | 2/2013 | Yuen et al. |
| 8,398,538 B2 | 3/2013 | Dothie |
| 8,403,865 B2 | 3/2013 | Halperin et al. |
| 8,413,274 B2 | 4/2013 | Weismiller et al. |
| 8,421,606 B2 | 4/2013 | Collins, Jr. et al. |
| 8,428,696 B2 | 4/2013 | Foo |
| 8,444,558 B2 | 5/2013 | Young et al. |
| 8,517,953 B2 | 8/2013 | Lange et al. |
| 8,620,615 B2 | 12/2013 | Oexman |
| 8,672,853 B2 | 3/2014 | Young |
| 8,679,034 B2 | 3/2014 | Halperin et al. |
| 8,769,747 B2 | 7/2014 | Mahoney et al. |
| 8,840,564 B2 | 9/2014 | Pinhas et al. |
| 8,909,357 B2 | 12/2014 | Rawls-Meehan |
| 8,931,329 B2 | 1/2015 | Mahoney et al. |
| 8,966,689 B2 | 3/2015 | McGuire et al. |
| 8,973,183 B1 | 3/2015 | Palashewski et al. |
| 8,984,687 B2 | 3/2015 | Stusynski et al. |
| 2002/0124311 A1 | 9/2002 | Peftoulidis |
| 2002/0184711 A1 | 12/2002 | Mahoney et al. |
| 2002/0189621 A1 | 12/2002 | Ek |
| 2003/0045806 A1 | 3/2003 | Brydon |
| 2003/0128125 A1* | 7/2003 | Burbank et al. ............... 340/605 |
| 2003/0163874 A1 | 9/2003 | Boso et al. |
| 2003/0166995 A1 | 9/2003 | Jansen |
| 2003/0182728 A1 | 10/2003 | Chapman et al. |
| 2003/0221261 A1 | 12/2003 | Torbet et al. |
| 2004/0049132 A1 | 3/2004 | Barron et al. |
| 2005/0022606 A1 | 2/2005 | Partin et al. |
| 2005/0038326 A1 | 2/2005 | Mathur |
| 2005/0115561 A1* | 6/2005 | Stahmann et al. ....... 128/200.24 |
| 2005/0190065 A1 | 9/2005 | Ronholm |
| 2005/0190068 A1 | 9/2005 | Gentry et al. |
| 2005/0283039 A1 | 12/2005 | Cornel |
| 2006/0020178 A1 | 1/2006 | Sotos et al. |
| 2006/0031996 A1 | 2/2006 | Rawls-Meehan |
| 2006/0047217 A1 | 3/2006 | Mirtalebi |
| 2006/0152378 A1 | 7/2006 | Lokhorst |
| 2006/0162074 A1 | 7/2006 | Bader |
| 2007/0049842 A1 | 3/2007 | Hill et al. |
| 2007/0118054 A1 | 5/2007 | Pinhas et al. |
| 2007/0149883 A1 | 6/2007 | Yesha |
| 2007/0179334 A1 | 8/2007 | Groves et al. |
| 2007/0180047 A1 | 8/2007 | Dong et al. |
| 2007/0180618 A1 | 8/2007 | Weismiller et al. |
| 2007/0276202 A1 | 11/2007 | Raisanen et al. |
| 2008/0052837 A1 | 3/2008 | Blumberg |
| 2008/0071200 A1 | 3/2008 | Rawls-Meehan |
| 2008/0077020 A1 | 3/2008 | Young et al. |
| 2008/0092291 A1 | 4/2008 | Rawls-Meehan |
| 2008/0092292 A1 | 4/2008 | Rawls-Meehan |
| 2008/0092293 A1 | 4/2008 | Rawls-Meehan |
| 2008/0092294 A1 | 4/2008 | Rawls-Meehan |
| 2008/0093784 A1 | 4/2008 | Rawls-Meehan |
| 2008/0097774 A1 | 4/2008 | Rawls-Meehan |
| 2008/0097778 A1 | 4/2008 | Rawls-Meehan |
| 2008/0097779 A1 | 4/2008 | Rawls-Meehan |
| 2008/0104750 A1 | 5/2008 | Rawls-Meehan |
| 2008/0104754 A1 | 5/2008 | Rawls-Meehan |
| 2008/0104755 A1 | 5/2008 | Rawls-Meehan |
| 2008/0104756 A1 | 5/2008 | Rawls-Meehan |
| 2008/0104757 A1 | 5/2008 | Rawls-Meehan |
| 2008/0104758 A1 | 5/2008 | Rawls-Meehan |
| 2008/0104759 A1 | 5/2008 | Rawls-Meehan |
| 2008/0104760 A1 | 5/2008 | Rawls-Meehan |
| 2008/0104761 A1 | 5/2008 | Rawls-Meehan |
| 2008/0109959 A1 | 5/2008 | Rawls-Meehan |
| 2008/0109964 A1 | 5/2008 | Flocard et al. |
| 2008/0109965 A1 | 5/2008 | Mossbeck |
| 2008/0115272 A1 | 5/2008 | Rawls-Meehan |
| 2008/0115273 A1 | 5/2008 | Rawls-Meehan |
| 2008/0115274 A1 | 5/2008 | Rawls-Meehan |
| 2008/0115275 A1 | 5/2008 | Rawls-Meehan |
| 2008/0115276 A1 | 5/2008 | Rawls-Meehan |
| 2008/0115277 A1 | 5/2008 | Rawls-Meehan |
| 2008/0115278 A1 | 5/2008 | Rawls-Meehan |
| 2008/0115279 A1 | 5/2008 | Rawls-Meehan |
| 2008/0115280 A1 | 5/2008 | Rawls-Meehan |
| 2008/0115281 A1 | 5/2008 | Rawls-Meehan |
| 2008/0115282 A1 | 5/2008 | Rawls-Meehan |
| 2008/0120775 A1 | 5/2008 | Rawls-Meehan |
| 2008/0120776 A1 | 5/2008 | Rawls-Meehan |
| 2008/0120777 A1 | 5/2008 | Rawls-Meehan |
| 2008/0120778 A1 | 5/2008 | Rawls-Meehan |
| 2008/0120779 A1 | 5/2008 | Rawls-Meehan |
| 2008/0120784 A1 | 5/2008 | Warner et al. |
| 2008/0122616 A1 | 5/2008 | Warner |
| 2008/0126122 A1 | 5/2008 | Warner et al. |
| 2008/0126132 A1 | 5/2008 | Warner |
| 2008/0127418 A1 | 6/2008 | Rawls-Meehan |
| 2008/0127424 A1 | 6/2008 | Rawls-Meehan |
| 2008/0147442 A1 | 6/2008 | Warner et al. |
| 2008/0162171 A1 | 7/2008 | Rawls-Meehan |
| 2008/0262657 A1 | 10/2008 | Howell et al. |
| 2008/0275314 A1 | 11/2008 | Mack et al. |
| 2008/0281611 A1 | 11/2008 | Rawls-Meehan |
| 2008/0281612 A1 | 11/2008 | Rawls-Meehan |
| 2008/0281613 A1 | 11/2008 | Rawls-Meehan |
| 2008/0288272 A1 | 11/2008 | Rawls-Meehan |
| 2008/0288273 A1 | 11/2008 | Rawls-Meehan |
| 2008/0306351 A1 | 12/2008 | Izumi |
| 2008/0307582 A1 | 12/2008 | Flocard et al. |
| 2009/0018853 A1 | 1/2009 | Rawls-Meehan |
| 2009/0018854 A1 | 1/2009 | Rawls-Meehan |
| 2009/0018855 A1 | 1/2009 | Rawls-Meehan |
| 2009/0018856 A1 | 1/2009 | Rawls-Meehan |
| 2009/0018857 A1 | 1/2009 | Rawls-Meehan |
| 2009/0018858 A1 | 1/2009 | Rawls-Meehan |
| 2009/0024406 A1 | 1/2009 | Rawls-Meehan |
| 2009/0037205 A1 | 2/2009 | Rawls-Meehan |
| 2009/0043595 A1 | 2/2009 | Rawls-Meehan |
| 2009/0064420 A1 | 3/2009 | Rawls-Meehan |
| 2009/0100599 A1 | 4/2009 | Rawls-Meehan |
| 2009/0121660 A1 | 5/2009 | Rawls-Meehan |
| 2009/0139029 A1 | 6/2009 | Rawls-Meehan |
| 2009/0203972 A1 | 8/2009 | Heneghan et al. |
| 2009/0275808 A1 | 11/2009 | DiMaio et al. |
| 2009/0314354 A1 | 12/2009 | Chaffee |
| 2010/0025900 A1 | 2/2010 | Rawls-Meehan |
| 2010/0090383 A1 | 4/2010 | Rawls-Meehan |
| 2010/0094139 A1 | 4/2010 | Brauers et al. |
| 2010/0099954 A1 | 4/2010 | Dickinson et al. |
| 2010/0152546 A1 | 6/2010 | Behan et al. |
| 2010/0170043 A1 | 7/2010 | Young et al. |
| 2010/0170044 A1 | 7/2010 | Kao et al. |
| 2010/0174198 A1 | 7/2010 | Young et al. |
| 2010/0174199 A1 | 7/2010 | Young et al. |
| 2010/0191136 A1 | 7/2010 | Wolford |
| 2010/0199432 A1 | 8/2010 | Rawls-Meehan |
| 2010/0231421 A1 | 9/2010 | Rawls-Meehan |
| 2010/0302044 A1 | 12/2010 | Chacon et al. |
| 2010/0317930 A1 | 12/2010 | Oexman et al. |
| 2011/0001622 A1 | 1/2011 | Gentry et al. |
| 2011/0010014 A1 | 1/2011 | Oexman et al. |
| 2011/0015495 A1 | 1/2011 | Dothie et al. |

(56) References Cited

U.S. PATENT DOCUMENTS

| | | | |
|---|---|---|---|
| 2011/0041592 A1 | 2/2011 | Schmoeller et al. |
| 2011/0068935 A1 | 3/2011 | Riley et al. |
| 2011/0087113 A1 | 4/2011 | Mack et al. |
| 2011/0094041 A1 | 4/2011 | Rawls-Meehan |
| 2011/0115635 A1 | 5/2011 | Petrovski et al. |
| 2011/0138539 A1 | 6/2011 | Mahoney et al. |
| 2011/0144455 A1 | 6/2011 | Young et al. |
| 2011/0156915 A1 | 6/2011 | Brauers et al. |
| 2011/0224510 A1 | 9/2011 | Oakhill |
| 2011/0239374 A1 | 10/2011 | Rawls-Meehan |
| 2011/0252569 A1 | 10/2011 | Rawls-Meehan |
| 2011/0258784 A1 | 10/2011 | Rawls-Meehan |
| 2011/0282216 A1 | 11/2011 | Shinar et al. |
| 2011/0283462 A1 | 11/2011 | Rawls-Meehan |
| 2011/0291795 A1 | 12/2011 | Rawls-Meehan |
| 2011/0291842 A1 | 12/2011 | Oexman |
| 2011/0295083 A1* | 12/2011 | Doelling et al. ............ 600/301 |
| 2011/0302720 A1 | 12/2011 | Yakam et al. |
| 2011/0306844 A1 | 12/2011 | Young |
| 2012/0017371 A1 | 1/2012 | Pollard |
| 2012/0025992 A1 | 2/2012 | Tallent et al. |
| 2012/0053423 A1 | 3/2012 | Kenalty et al. |
| 2012/0053424 A1 | 3/2012 | Kenalty et al. |
| 2012/0056729 A1 | 3/2012 | Rawls-Meehan |
| 2012/0057685 A1 | 3/2012 | Rawls-Meehan |
| 2012/0090698 A1 | 4/2012 | Giori et al. |
| 2012/0110738 A1 | 5/2012 | Rawls-Meehan |
| 2012/0110739 A1 | 5/2012 | Rawls-Meehan |
| 2012/0110740 A1 | 5/2012 | Rawls-Meehan |
| 2012/0112890 A1 | 5/2012 | Rawls-Meehan |
| 2012/0112891 A1 | 5/2012 | Rawls-Meehan |
| 2012/0112892 A1 | 5/2012 | Rawls-Meehan |
| 2012/0116591 A1 | 5/2012 | Rawls-Meehan |
| 2012/0119886 A1 | 5/2012 | Rawls-Meehan |
| 2012/0119887 A1 | 5/2012 | Rawls-Meehan |
| 2012/0138067 A1* | 6/2012 | Rawls-Meehan ............ 128/845 |
| 2012/0154155 A1 | 6/2012 | Brasch |
| 2012/0186019 A1 | 7/2012 | Rawls-Meehan |
| 2012/0198632 A1 | 8/2012 | Rawls-Meehan |
| 2012/0204887 A1 | 8/2012 | Connor |
| 2012/0240340 A1 | 9/2012 | Driscoll et al. |
| 2012/0304391 A1 | 12/2012 | Driscoll et al. |
| 2012/0311790 A1 | 12/2012 | Nomura et al. |
| 2013/0160212 A1 | 6/2013 | Oexman et al. |
| 2013/0174347 A1 | 7/2013 | Oexman et al. |
| 2013/0227787 A1 | 9/2013 | Herbst et al. |
| 2014/0007656 A1 | 1/2014 | Mahoney |
| 2014/0047644 A1 | 2/2014 | Mossbeck |
| 2014/0137332 A1 | 5/2014 | McGuire et al. |
| 2014/0182061 A1 | 7/2014 | Zaiss |
| 2014/0250597 A1 | 9/2014 | Chen et al. |
| 2014/0257571 A1 | 9/2014 | Chen et al. |
| 2014/0259418 A1 | 9/2014 | Nunn et al. |
| 2014/0259419 A1 | 9/2014 | Stusynski |
| 2014/0259431 A1 | 9/2014 | Fleury |
| 2014/0259433 A1* | 9/2014 | Nunn et al. ................ 5/713 |
| 2014/0259434 A1* | 9/2014 | Nunn et al. ................ 5/713 |
| 2014/0277611 A1 | 9/2014 | Nunn et al. |
| 2014/0277778 A1 | 9/2014 | Nunn et al. |
| 2014/0277822 A1 | 9/2014 | Nunn et al. |
| 2014/0313700 A1 | 10/2014 | Connell et al. |
| 2015/0025327 A1 | 1/2015 | Young et al. |
| 2015/0026896 A1 | 1/2015 | Fleury et al. |
| 2015/0136146 A1* | 5/2015 | Hood et al. ................ 128/845 |
| 2015/0157137 A1 | 6/2015 | Nunn et al. |
| 2015/0157519 A1 | 6/2015 | Stusynski et al. |
| 2015/0182033 A1 | 7/2015 | Brosnan et al. |
| 2015/0182397 A1 | 7/2015 | Palashewski et al. |
| 2015/0182399 A1 | 7/2015 | Palashewski et al. |
| 2015/0182418 A1 | 7/2015 | Zaiss |

FOREIGN PATENT DOCUMENTS

| | | |
|---|---|---|
| JP | 2004-229875 A | 8/2004 |
| WO | WO-2004/082549 A1 | 9/2004 |
| WO | WO 2008/128250 | 10/2008 |
| WO | WO-2009/108228 A1 | 9/2009 |
| WO | WO 2009/123641 | 10/2009 |
| WO | WO 2010/149788 | 12/2010 |

OTHER PUBLICATIONS

U.S. Appl. No. 14/146,281, filed Jan. 2, 2014, Palashewski et al.
U.S. Appl. No. 14/146,327, filed Jan. 2, 2014, Palashewski et al.
"International Application Serial No. PCT/US2014/024891, International Search Report mailed May 15, 2014", 4 pgs.
"International Application Serial No. PCT/US2014/024891, Written Opinion mailed May 15, 2014", 4 pgs.
"International Application Serial No. PCT/US2014/026288, International Search Report mailed May 15, 2014", 4 pgs.
"International Application Serial No. PCT/US2014/026288, Written Opinion mailed May 15, 2014", 4 pgs.
"International Application Serial No. PCT/US2014/026526, International Search Report mailed May 15, 2014", 3 pgs.
"International Application Serial No. PCT/US2014/026526, Written Opinion mailed May 15, 2014", 4 pgs.
International Application Serial No. PCT/US2014/027752, International Search Report mailed Jul. 15, 2014, 5 pages.
International Application Serial No. PCT/US2014/026568, International Search Report mailed May 26, 2014, 3 pages.
International Application Serial No. PCT/US2014/026390, International Search Report mailed May 26, 2014, 4 pages.
International Application Serial No. PCT/US2014/026347, International Search Report mailed Jun. 27, 2014, 6 pages.
International Preliminary Report on Patentability and Written Opinion in International Application No. PCT/US2014/024891, dated Sep. 15, 2015, 5 pages.
International Preliminary Report on Patentability and Written Opinion in International Application No. PCT/US2014/026347, dated Sep. 15, 2015, 8 pages.
International Preliminary Report on Patentability and Written Opinion in International Application No. PCT/US2014/026526, dated Sep. 24, 2015, 6 pages.
International Preliminary Report on Patentability and Written Opinion in International Application No. PCT/US2014/026568, dated Sep. 24, 2015, 6 pages.
International Preliminary Report on Patentability and Written Opinion in International Application No. PCT/US2014/027752, dated Sep. 15, 2015, 6 pages.
International Preliminary Report on Patentability and Written Opinion in International Application No. PCT/US2014/028137, dated Sep. 24, 2015, 6 pages.
International Search Report in International Application No. PCT/US2014/028137, dated Jul. 7, 2014, 2 pages.
U.S. Appl. No. 14/687,633, filed Apr. 15, 2015, Brosnan et al.
U.S. Appl. No. 14/675,355, filed Mar. 31, 2015, Palashewski et al.
U.S. Appl. No. 14/283,675, filed May 21, 2014, Mahoney et al.

* cited by examiner

INFLATABLE AIR MATTRESS SNORING DETECTION AND RESPONSE

CROSS-REFERENCES

This application claims the benefit of priority to U.S. Provisional Application No. 61/782,394, filed on Mar. 14, 2013, the disclosure of which is incorporated herein in its entirety by reference.

The subject matter described in this application is related to subject matter disclosed in the following applications: U.S. Application Ser. No. 61/781,266, filed on Mar. 14, 2013, entitled "INFLATABLE AIR MATTRESS ALARM AND MONITORING SYSTEM"; U.S. Application Ser. No. 61/781,503, filed on Mar. 14, 2013, entitled "INFLATABLE AIR MATTRESS SYSTEM ARCHITECTURE"; U.S. Application Ser. No. 61/781,541, filed on Mar. 14, 2013, entitled "INFLATABLE AIR MATTRESS AUTOFILL AND OFF BED PRESSURE ADJUSTMENT"; U.S. Application Ser. No. 61/781,571, filed on Mar. 14, 2013, entitled "INFLATABLE AIR MATTRESS SLEEP ENVIRONMENT ADJUSTMENT AND SUGGESTIONS"; U.S. Application Ser. No. 61/781,296, filed on Mar. 14, 2013, entitled "INFLATABLE AIR MATTRESS WITH LIGHT AND VOICE CONTROLS"; U.S. Application Ser. No. 61/781,311, filed on Mar. 14, 2013, entitled "INFLATABLE AIR MATTRESS SYSTEM WITH DETECTION TECHNIQUES." The contents of each of the above-referenced U.S. patent applications are herein incorporated by reference in their entirety.

TECHNICAL FIELD

This patent document pertains generally to mattress systems and more particularly, but not by way of limitation, to an inflatable air mattress system.

BACKGROUND

Air bed systems, such as the one described in U.S. Pat. No. 5,904,172 which is incorporated herein by reference in its entirety, generally allow a user to select a desired pressure for each air chamber within the mattress. Upon selecting the desired pressure, a signal is sent to a pump and valve assembly in order to inflate or deflate the air bladders as necessary in order to achieve approximately the desired pressure within the air bladders.

In various examples, an air mattress control system allows a user to adjust the firmness or position of an air mattress bed. The mattress may have more than one zone thereby allowing a left and right side of the mattress to be adjusted to different firmness levels. Additionally, the bed may be adjustable to different positions. For example, the head section of the bed may be raised up while the foot section of the bed stays in place. In various examples, two separate remote controls are used to adjust the position and firmness, respectively.

A common problem experienced by many people is snoring. Snoring can not only result in poor sleep quality and potential health issues, but it can also disturb another person who is sleeping in the same room, such as a spouse sleeping in the same bed. Some people deal with the problem by waking the snorer up in order to stop the snoring. However, the snorer often begins snoring again after going back to sleep. Moreover, waking the snorer also interrupts the snorer's sleep.

BRIEF DESCRIPTION OF DRAWINGS

Some embodiments are illustrated by way of example and not limitation in the figures of the accompanying drawings in which.

DETAILED DESCRIPTION

Figure 1:
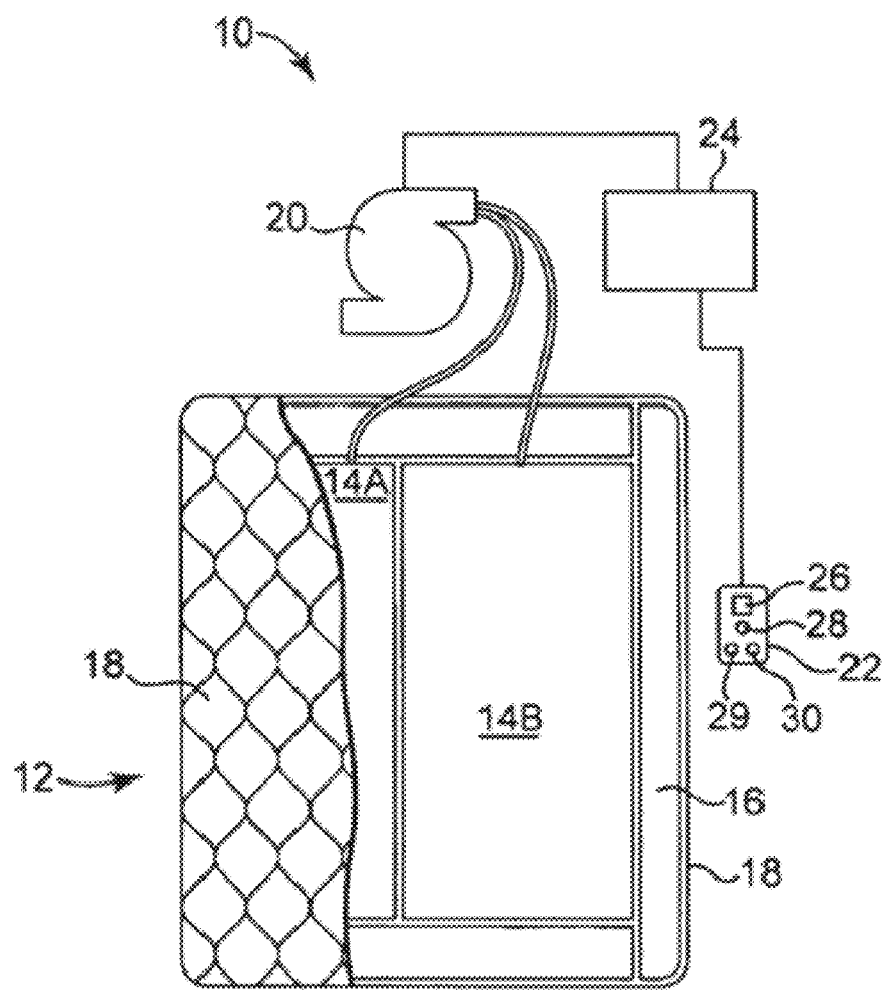
FIG. 1 is a diagrammatic representation of an air bed system, according to an example.

FIG. 1 is a diagrammatic representation of an air bed system 10 in an example embodiment. The system 10 can include a bed 12, which can comprise at least one air chamber 14 surrounded by a resilient border 16 and encapsulated by bed ticking 18. The resilient border 16 can comprise any suitable material, such as foam.

As illustrated in FIG. 1, the bed 12 can be a two chamber design having a first air chamber 14A and a second air chamber 14B. The first and second air chambers 14A and 14B can be in fluid communication with a pump 20. The pump 20 can be in electrical communication with a remote control 22 via a control box 24. The remote control 22 can communicate via wired or wireless means with the control box 24. The control box 24 can be configured to operate the pump 20 to cause increases and decreases in the fluid pressure of the first and second air chambers 14A and 14B based upon commands input by a user through the remote control 22. The remote control 22 can include a display 26, output selecting means 28, a pressure increase button 29, and a pressure decrease button 30. The output selecting means 28 can allow the user to switch the pump output between the first and second air chambers 14A and 14B, thus enabling control of multiple air chambers with a single remote control 22. For example, output selecting means may by a physical control (e.g., switch or button) or an input control displayed on the display 26. Alternatively, separate remote control units can be provided for each air chamber and may each include the ability to control multiple air chambers. The pressure increase and decrease buttons 29 and 30 can allow a user to increase or decrease the pressure, respectively, in the air chamber selected with the output selecting means 28. Adjusting the pressure within the selected air chamber can cause a corresponding adjustment to the firmness of the air chamber.

Figure 2:
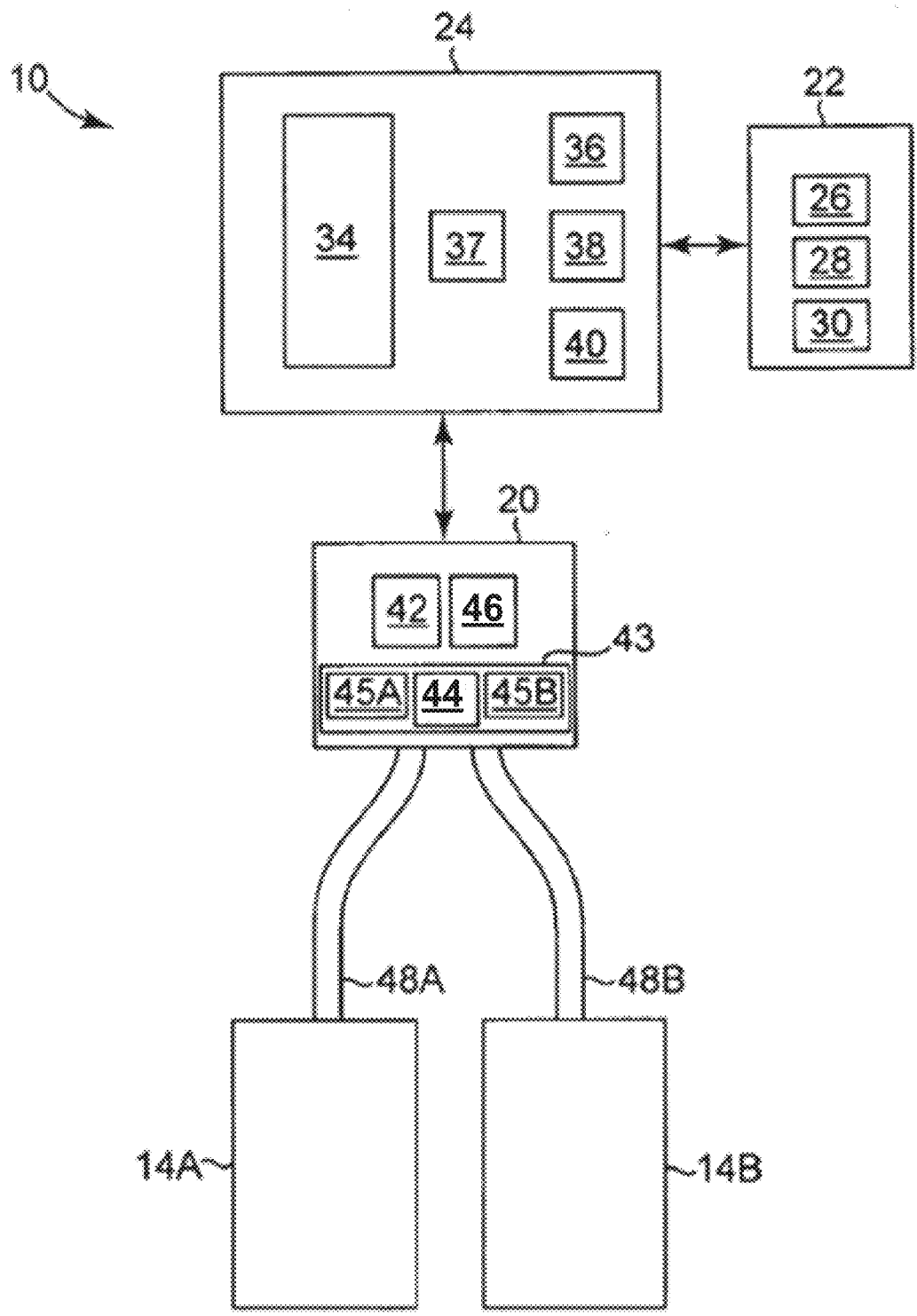
FIG. 2 is a block diagram of various components of the air bed system of FIG. 1, according to an example.

FIG. 2 is a block diagram detailing data communication between certain components of the air bed system 10 according to various examples. As shown in FIG. 2, the control box 24 can include a power supply 34, a processor 36, memory 37, a switching means 38, and an analog to digital (A/D) converter 40. The switching means 38 can be, for example, a relay or a solid state switch. The switching means 38 can be located in the pump 20 rather than the control box 24.

The pump 20 and the remote control 22 can be in two-way communication with the control box 24. The pump 20 can include a motor 42, a pump manifold 43, a relief valve 44, a first control valve 45A, a second control valve 45B, and a pressure transducer 46, and can be fluidly connected with the first air chamber 14A and the second air chamber 14B via a first tube 48A and a second tube 48B, respectively. The first and second control valves 45A and 45B can be controlled by the switching means 38, and can be operable to regulate the flow of fluid between the pump 20 and the first and second air chambers 14A and 14B, respectively.

In an example, the pump 20 and the control box 24 can be provided and packaged as a single unit. Alternatively, the pump 20 and the control box 24 can be provided as physically separate units.

In operation, the power supply 34 can receive power, such as 110 VAC power, from an external source and can convert the power to various forms required by certain components of the air bed system 10. The processor 36 can be used to control various logic sequences associated with operation of the air bed system 10, as will be discussed in further detail below.

The example of the air bed system 10 shown in FIG. 2 contemplates two air chambers 14A and 14B and a single pump 20. However, other examples may include an air bed system having two or more air chambers and one or more pumps incorporated into the air bed system to control the air chambers. In an example, a separate pump can be associated with each air chamber of the air bed system or a pump may be associated with multiple chambers of the air bed system. Separate pumps can allow each air chamber to be inflated or deflated independently and simultaneously. Furthermore, additional pressure transducers can also be incorporated into the air bed system such that, for example, a separate pressure transducer can be associated with each air chamber. Additionally, one or both of the chambers 14A and 14B can include multiple separate bladders or "zones" within the chamber, such as one bladder for the head and one bladder for the body.

In the event that the processor 36 sends a decrease pressure command to one of the air chambers 14A or 14B, the switching means 38 can be used to convert the low voltage command signals sent by the processor 36 to higher operating voltages sufficient to operate the relief valve 44 of the pump 20 and open the control valves 45A or 45B. Opening the relief valve 44 can allow air to escape from the air chamber 14A or 14B through the respective air tube 48A or 48B. During deflation, the pressure transducer 46 can send pressure readings to the processor 36 via the A/D converter 40. The A/D converter 40 can receive analog information from the pressure transducer 46 and can convert the analog information to digital information useable by the processor 36. The processor 36 may send the digital signal to the remote control 22 to update the display 26 on the remote control in order to convey the pressure information to the user.

In the event that the processor 36 sends an increase pressure command, the pump motor 42 can be energized, sending air to the designated air chamber through the air tube 48A or 48B via electronically operating the corresponding valve 45A or 45B. While air is being delivered to the designated air chamber in order to increase the firmness of the chamber, the pressure transducer 46 can sense pressure within the pump manifold 43. Again, the pressure transducer 46 can send pressure readings to the processor 36 via the A/D converter 40. The processor 36 can use the information received from the A/D converter 40 to determine the difference between the actual pressure in the air chamber 14A or 14B and the desired pressure. The processor 36 can send the digital signal to the remote control 22 to update the display 26 on the remote control in order to convey the pressure information to the user.

Generally speaking, during an inflation or deflation process, the pressure sensed within the pump manifold 43 provides an approximation of the pressure within the air chamber. An example method of obtaining a pump manifold pressure reading that is substantially equivalent to the actual pressure within an air chamber is to turn off the pump 20, allow the pressure within the air chamber 14A or 14B and the pump manifold 43 to equalize, and then sense the pressure within the pump manifold 43 with the pressure transducer 46. Thus, providing a sufficient amount of time to allow the pressures within the pump manifold 43 and the chamber 14A or 14B to equalize may result in pressure readings that are accurate approximations of the actual pressure within the air chamber 14A or 14B. In various examples, the pressure of 48A/B is continuously monitored using multiple pressure sensors.

In an example, another method of obtaining a pump manifold pressure reading that is substantially equivalent to the actual pressure within an air chamber is through the use of a pressure adjustment algorithm. In general, the method can function by approximating the air chamber pressure based upon a mathematical relationship between the air chamber pressure and the pressure measured within the pump manifold 43 (during both an inflation cycle and a deflation cycle), thereby eliminating the need to turn off the pump 20 in order to obtain a substantially accurate approximation of the air chamber pressure. As a result, a desired pressure setpoint within the air chamber 14A or 14B can be achieved without the need for turning the pump 20 off to allow the pressures to equalize. The latter method of approximating an air chamber pressure using mathematical relationships between the air chamber pressure and the pump manifold pressure is described in detail in U.S. application Ser. No. 12/936,084, the entirety of which is incorporated herein by reference.

Figure 3:
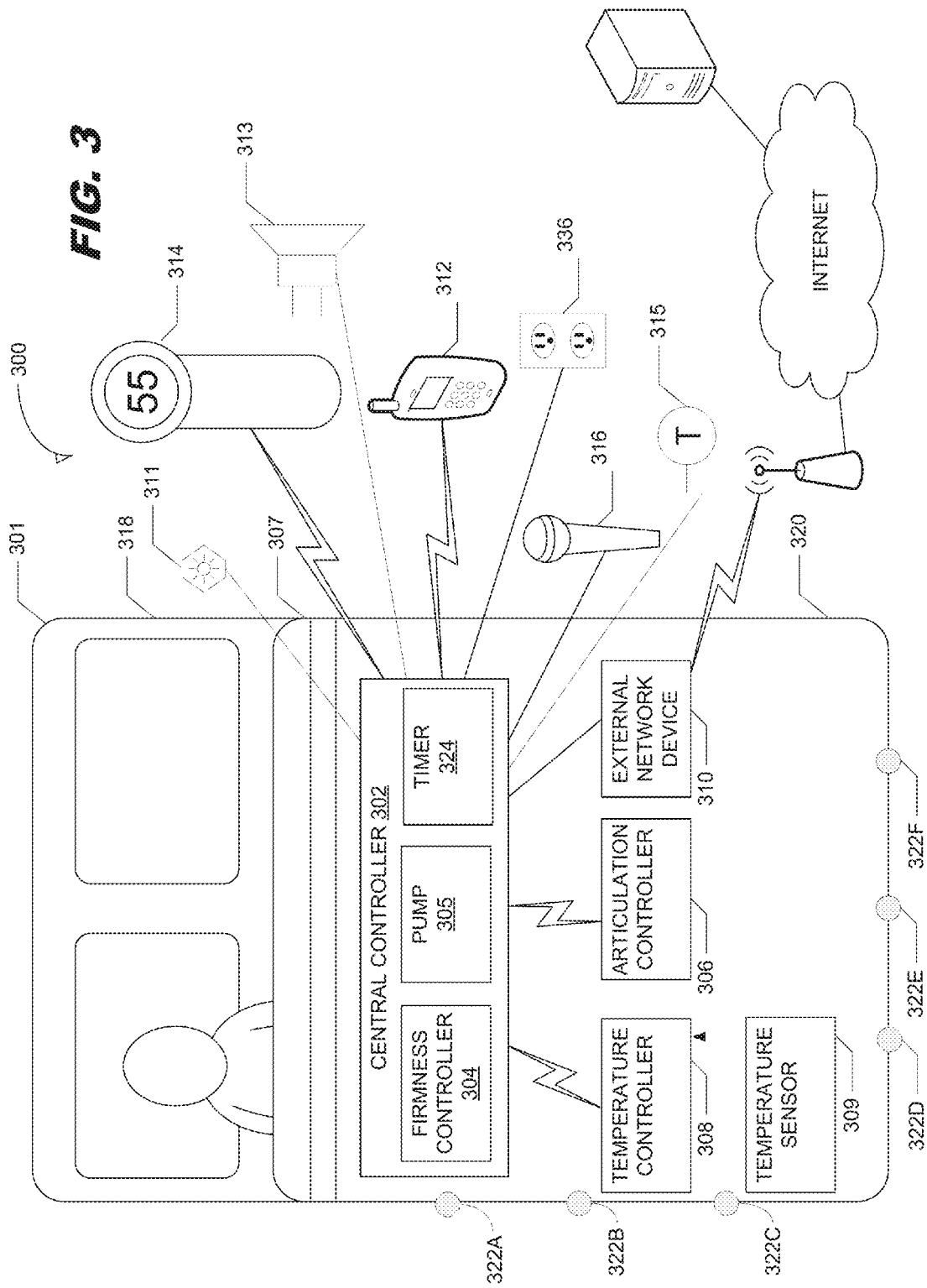
FIG. 3 is a block diagram of an air bed system architecture, according to an example.

FIG. 3 illustrates an example air bed system architecture 300. The architecture 300 includes a bed 301, e.g., an inflatable air mattress, a central controller 302, a firmness controller 304, an articulation controller 306, a temperature controller 308 in communication with one or more temperature sensors 309, an external network device 310, remote controllers 312, 314, and a voice controller 316. In addition to providing for the input of vocal commands, the voice controller 316 can also be used for detecting snoring of a sleeper as described in further detail below. Thus, the voice controller 316 can include any detection means capable of detecting sound waves, such as a microphone. While described as using an air bed, the system architecture may also be used with other types of beds.

As illustrated in FIG. 3, the central controller 302 includes the firmness controller 304 and a pump 305. The system architecture 300 is configured as a star topology with the central controller 302 and the firmness controller 304 functioning as the hub and the articulation controller 306, the temperature controller 308, the external network device 310, the remote controllers 312, 314, and the voice controller 316 functioning as possible spokes, also referred to herein as components. Thus, in various examples, the central controller 302 acts a relay between the various components.

In yet another example, central controller 302 listens to communications (e.g., control signals) between components even if the communication is not being relayed through central controller 302. For example, consider a user sending a command using remote 312 to temperature controller 308. Central controller 302 may listen for the command and check to determine if instructions are stored at central controller 302 to override the command (e.g., it conflicts with a previous setting). Central controller 302 may also log the command for future use (e.g., determining a pattern of user preferences for the components).

In other examples, different topologies may be used. For example, the components and the central controller 302 may be configured as a mesh network in which each component may communicate with one or all of the other components directly, bypassing the central controller 302. In various examples, a combination of topologies may be used. For example, the remote controller 312 may communicate directly to the temperature controller 308 but also relay the communication to the central controller 302.

In various examples, the controllers and devices illustrated in FIG. 3 may each include a processor, a storage device, and a network interface. The processor may be a general purpose central processing unit (CPU) or application-specific integrated circuit (ASIC). The storage device may include volatile or non-volatile static storage (e.g., Flash memory, RAM, EPROM, etc.). The storage device may store instructions which, when executed by the processor, configure the processor to perform the functionality described herein. For example, a processor of the firmness controller 304 may be configured to send a command to a relief valve to decrease the pressure in a bed.

In various examples, the network interface of the components may be configured to transmit and receive communications in a variety of wired and wireless protocols. For example, the network interface may be configured to use the 802.11 standards (e.g., 802.11a/b/c/g/n/ac), PAN network standards such as 802.15.4 or Bluetooth, infrared, cellular standards (e.g., 3G/4G etc.), Ethernet, and USB for receiving and transmitting data. The previous list is not intended to be exhaustive and other protocols may be used. Not all components of FIG. 3 need to be configured to use the same protocols. For example, the remote controller 312 may communicate with the central controller 302 via Bluetooth while the temperature controller 308 and the articulation controller 306 are connected to the central controller using 802.15.4. Within FIG. 3, the lightning connectors represent wireless connections and the solid lines represent wired connections, however, the connections between the components is not limited to such connections and each connection may be wired or wireless. For example, the voice controller 316 can be connected wirelessly to the central controller 302.

Moreover, in various examples, the processor, storage device, and network interface of a component may be located in different locations than various elements used to effect a command. For example, as in FIG. 1, the firmness controller 302 may have a pump that is housed in a separate enclosure than the processor used to control the pump. Similar separation of elements may be employed for the other controllers and devices in FIG. 3.

In various examples, the firmness controller 304 is configured to regulate pressure in an air mattress. For example, the firmness controller 304 may include a pump such as described with reference to FIG. 2 (see e.g., pump 20). Thus, in an example, the firmness controller 304 may respond to commands to increase or decrease pressure in the air mattress. The commands may be received from another component or based on stored application instructions that are part of the firmness controller 304.

As illustrated in FIG. 3, the central controller 302 includes the firmness controller 304. Thus, in an example, the processor of the central controller 302 and the firmness controller 304 may be the same processor. Furthermore, the pump may also be part of the central controller 302. Accordingly, the central controller 302 may be responsible for pressure regulation as well as other functionality as described in further portions of this disclosure.

In various examples, the articulation controller 306 is configured to adjust the position of a bed mattress (e.g., bed 301) by adjusting a foundation 307 that supports the bed mattress. In an example, the bed 301 can include a single foundation 307 configured to adjust the position of a bed having a single mattress. In another example, the bed 301 can include two side-by-side foundations 307 configured to operate in tandem to adjust the position of a bed having a single mattress. In yet another example, the bed 301 can include two side-by-side mattresses supported by two side-by-side foundations 307, wherein the foundations 307 are operable independently such that separate positions may be set for the two different mattresses of the bed 301. The foundation 307 may include more than one zone, e.g., a head portion 318 and a foot portion 320, which may be independently adjusted. The articulation controller 306 may also be configured to provide different levels of massage to a person on the bed.

In various examples, the temperature controller 308 is configured to increase, decrease, or maintain the temperature of a user. For example, a pad may be placed on top of or be part of the air mattress. Air may be pushed through the pad and vented to cool off a user of the bed. Conversely, the pad may include a heating element that may be used to keep the user warm. In various examples, the pad includes the temperature sensor 309 and the temperature controller 308 receives temperature readings from the temperature sensor 309. In other examples, the temperature sensor 309 can be separate from the pad, e.g., part of the air mattress or foundation. Alternatively or in addition, a blanket can be provided having similar functionality to the pad.

In various examples, additional controllers may communicate with the central controller 302. These controllers may include, but are not limited to, illumination controllers for controlling the power status (e.g., on or off) or intensity of light elements 311 and 322A-F placed on and around the bed, audio/visual controllers for controlling the power status or volume of one or more audio/visual components 313 located near the bed, thermostat controllers for controlling a temperature setting of a thermostat device 315, and outlet controllers for controlling power to one or more power outlets 336. In an example, the light elements 311 and 322A-F can be network controlled lights.

In various examples, the external network device 310, the remote controllers 312, 314 and the voice controller 316 may be used to input commands (e.g., from a user or remote system) to control one or more components of the system architecture 300. The commands may be transmitted from one of the controllers 312, 314, or 316 and received in the central controller 302. The central controller 302 may process the command to determine the appropriate component to route the received command. For example, each command sent via one of controllers 312, 314, or 316 may include a header or other metadata that indicates which component the command is for. The central controller 302 may then transmit the command via the central controller 302's network interface to the appropriate component.

For example, a user may input a desired temperature for the user's bed into the remote controller 312. The desired temperature may be encapsulated in a command data structure that includes the temperature as well as identifies the temperature controller 308 as the desired component to be controlled. The command data structure may then be transmitted via Bluetooth to the central controller 302. In various examples, the command data structure is encrypted before being transmitted. The central controller 302 may parse the command data structure and relay the command to the temperature controller 308 using a PAN. The temperature controller 308 may then configure its elements to increase or decrease the temperature of the pad depending on the temperature originally input into the remote controller 312.

In one example implementation, the central controller 302 can detect user presence using temperature changes detected in the mattress, e.g., using one or more temperature sensors positioned in or on the mattress. The temperature sensors and the central controller 302 can detect a rise in temperature, e.g., over a specified period of time, and determine that a user is present in the bed. For example, if the central controller 302 detects a rise in temperature and then determines that the detected rise in temperature was not caused by the system's temperature controller 308, the central controller 302 can determine that the user is present.

In various examples, data may be transmitted from a component back to one or more of the remote controllers. For example, the current temperature as determined by a sensor element of the temperature controller 308, e.g., the temperature sensor 309, the pressure of the bed, the current position of the foundation or other information may be transmitted to the central controller 302. The central controller 302 may then transmit the received information and transmit it to the remote controller 312 where it may be displayed to the user.

In various examples, multiple types of devices may be used to input commands to control the components of the architecture 300. For example, the remote controller 312 may be a mobile device such as a smart phone or tablet computer running an application. Other examples of the remote controller 312 may include a dedicated device for interacting with the components described herein. In various examples, the remote controllers 312/314 include a display device for displaying an interface to a user. The remote controller 312/314 may also include one or more input devices. Input devices may include, but are not limited to, keypads, touchscreen, gesture, motion and voice controls.

The remote controller 314 may be a single component remote configured to interact with one component of the mattress architecture. For example, the remote controller 314 may be configured to accept inputs to increase or decrease the air mattress pressure. The voice controller 316 may be configured to accept voice commands to control one or more components. In various examples, more than one of the remote controllers 312/314 and the voice controller 316 may be used.

With respect to the remote controller 312, the application may be configured to pair with one or more central controllers. For each central controller, data may be transmitted to the mobile device that includes a list of components linked with the central controller. For example, consider that the remote controller 312 is a mobile phone and that the application has been authenticated and paired with the central controller 302. The remote controller 312 may transmit a discovery request to the central controller 302 to inquire about other components and available services. In response, the central controller 302 may transmit a list of services that includes available functions for adjusting the firmness of the bed, position of the bed, and temperature of the bed. In various embodiments, the application may then display functions for increasing/decreasing pressure of the air mattress, adjusting positions of the bed, and adjusting temperature. If components are added/removed to the architecture under control of the central controller 302, an updated list may be transmitted to the remote controller 312 and the interface of the application may be adjusted accordingly.

In various examples, the central controller 302 is configured as a distributor of software updates to components in the architecture 300. For example, a firmware update for the temperature controller 308 may become available. The update may be loaded into a storage device of the central controller 302 (e.g., via a USB interface or using wireless techniques). In wireless applications, the central controller 302 may, for example, receive updates from the cloud either from wifi or from a mobile connection over Bluetooth. The central controller 302 may then transmit the update to the temperature controller 308 with instructions to update. The temperature controller 308 may attempt to install the update. A status message may be transmitted from the temperature controller 308 to the central controller 302 indicating the success or failure of the update.

In various examples, the central controller 302 is configured to analyze data collected by a pressure transducer (e.g., the transducer 46 with respect to FIG. 2) to determine various states of a person lying on the bed 301. For example, the central controller 302 may determine the heart rate, respiration rate, or movement of a person lying in the bed 301. Additional processing may be done using the collected data to determine a possible sleep state of the person. For example, the central controller 302 may determine when a person falls asleep and, while asleep, the various sleep states of the person. The collected data may also be used to determine when a person is snoring. In another example, rather than performing the data analysis in the central controller 302, a digital signal processor (DSP) can be provided to analyze the data collected by the pressure transducer. Alternatively, the data collected by the pressure transducer could be sent to a cloud-based computing system for remote analysis.

In various examples, the external network device 310 includes a network interface to interact with an external server for processing and storage of data related to components in the architecture 300. For example, the determined sleep data as described above may be transmitted via a network (e.g., the Internet) from the central controller 302 to the external network device 310 for storage. In an example, the pressure transducer data may be transmitted to the external server for additional analysis. The external network device 310 may also analyze and filter the data before transmitting it to the external server.

In an example, diagnostic data of the components may also be routed to the external network device 310 for storage and diagnosis on the external server. For example, if the temperature controller 308 detects an abnormal temperature reading (e.g., a drop in temperature over one minute that exceeds a set threshold) diagnostic data (sensor readings, current settings, etc.) may be wireless transmitted from the temperature controller 308 to the central controller 302. The central controller 302 may then transmit this data via USB to the external network device 310. The external network device 310 may wirelessly transmit the information to an WLAN access point where it is routed to the external server for analysis.

In one example, the bed system architecture 300 can include one or more bed lights 322A-322F (referred to collectively in this disclosure as "bed lights 322") to illuminate a portion of a room, e.g., when a user gets out of the bed 301. The lights 322 can be attached around the foundation 307, e.g., affixed to the foundation around its perimeter. In FIG. 3, the lights 322 are depicted as extending around two sides of the foundation 307. In other configurations, the lights 322 can extend around more than two sides of the foundation 307, or only a single side. In one example implementation, the lights 322 can be positioned underneath the foundation 307 to project light outwardly from the foundation 307. The bed system architecture 300 can also include one or more lights 311 that are not positioned on the bed, such as overhead lights or bedside lamps. The bed system architecture 300 can provide for the control of both the bed lights 322 and the surrounding room lights 311.

Example Machine Architecture and Machine-Readable Medium

Figure 4:
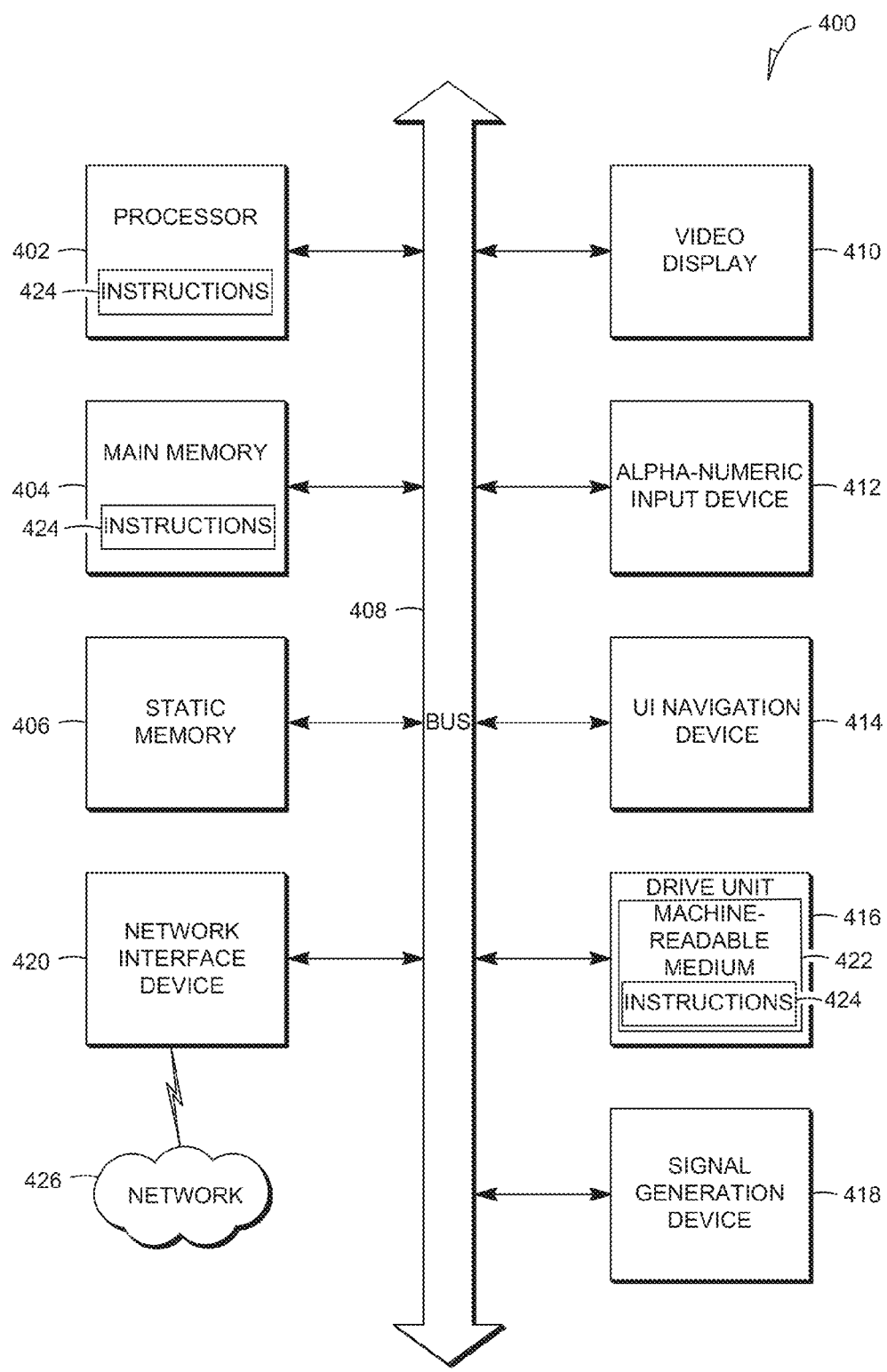
FIG. 4 is a block diagram of a machine in the example form of a computer system within which a set instructions, for causing the machine to perform any one or more of the methodologies discussed herein, may be executed.

FIG. 4 is a block diagram of a machine in the example form of a computer system 400 within which instructions, for causing the machine to perform any one or more of the methodologies discussed herein, may be executed. In alternative embodiments, the machine operates as a standalone device or may be connected (e.g., networked) to other machines. In a networked deployment, the machine may operate in the capacity of a server or a client machine in a server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 400 includes a processor 402 (e.g., a central processing unit (CPU), a graphics processing unit (GPU), ASIC or a combination), a main memory 404 and a static memory 406, which communicate with each other via a bus 408. The computer system 400 may further include a video display unit 410 (e.g., a liquid crystal display (LCD) or a cathode ray tube (CRT)). The computer system 400 also includes an alphanumeric input device 412 (e.g., a keyboard and/or touchscreen), a user interface (UI) navigation device 414 (e.g., a mouse), a disk drive unit 416, a signal generation device 418 (e.g., a speaker) and a network interface device 420.

Machine-Readable Medium

The disk drive unit 416 includes a machine-readable medium 422 on which is stored one or more sets of instructions and data structures (e.g., software) 424 embodying or utilized by any one or more of the methodologies or functions described herein. The instructions 424 may also reside, completely or at least partially, within the main memory 404 and/or within the processor 402 during execution thereof by the computer system 400, the main memory 404 and the processor 402 also constituting machine-readable media.

While the machine-readable medium 422 is shown in an example embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present invention, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks such as internal hard disks and removable disks; magneto-optical disks; and CD-ROM and DVD-ROM disks.

Transmission Medium

The instructions 424 may further be transmitted or received over a communications network 426 using a transmission medium. The instructions 424 may be transmitted using the network interface device 420 and any one of a number of well-known transfer protocols (e.g., HTTP). Examples of communication networks include a local area network ("LAN"), a wide area network ("WAN"), the Internet, mobile telephone networks, Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

Snoring Detection Techniques

In addition to the techniques described above, this disclosure is directed to techniques for detection of various aspects of a user of the system architecture 300. For example, and as described in further detail below, user snoring can be detected using various techniques described in this disclosure In a first technique for snoring detection, the system architecture 300 can detect biometric parameters of a user such as motion, respiration, and heartbeat. These biometric parameters can be detected both while the user is awake and while the user is sleeping. In various examples, the biometric parameters can be used to determine a sleep state of the user and whether the user is snoring. Techniques for monitoring a user's sleep using heart rate information, respiration rate information, and other user information are disclosed in U.S. Patent Application Publication No. 20100170043 to Steven J. Young et al., titled "APPARATUS FOR MONITORING VITAL SIGNS," the entire content of which is incorporated herein by reference. After snoring is detected, the system architecture 300 and, in particular, the central controller 302, can make one or more adjustments to the sleep environment or the bed 301 as will be discussed in further detail below. In an example, the user can instruct the system architecture 300 to monitor for snoring after the user falls asleep and to initiate specific changes to the sleep environment or the bed 301 upon detection of snoring. In another example, the system architecture 300 can automatically, e.g., without user instruction, monitor for snoring and determine what changes should be made, if any, to the sleep environment or the bed 301. In yet another example, when two users are lying on the bed 301 side-by-side, the system architecture 300 can determine which of the users is snoring and initiate the changes to that user's side of the bed.

In accordance with this disclosure, the central controller 302, or another processing means associated with the bed 301, can detect user sleeping motion, respiration, and heartbeat via pressure changes. For example, the pressure transducer 46 (of FIG. 2) can be used to monitor the air pressure in the air mattress of the bed 301. If the user on the air mattress is not moving, the air pressure changes in the mattress can be relatively minimal, and can be attributable to respiration and heartbeat. When the user on the air mattress is moving, however, the air pressure in the mattress can fluctuate by a much larger amount. Thus, the pressure signals generated by the pressure transducer 46 and received by the central controller 302 can be filtered and indicated as corresponding to motion, heartbeat, or respiration.

In one example implementation, the central controller 302 can execute instructions that cause the pressure transducer 46 to measure air pressure values at a predefined sample rate. The central controller 302 can store the pressure signals in a memory device. Processing of the pressure signals can be performed by the central controller 302, or at a location remote from the bed 301, such as on a processor of a smartphone, a mobile device, or a cloud-based computing system.

As indicated above, the central controller 302 can determine a user's sleep state, e.g., rapid eye movement ("REM") or non-rapid eye movement ("NREM"), by using one or more of the biometric parameters. In an example, the central controller 302 can execute instructions to monitor the snoring state of the user only after the user has reached a particular sleep state.

Figure 5:
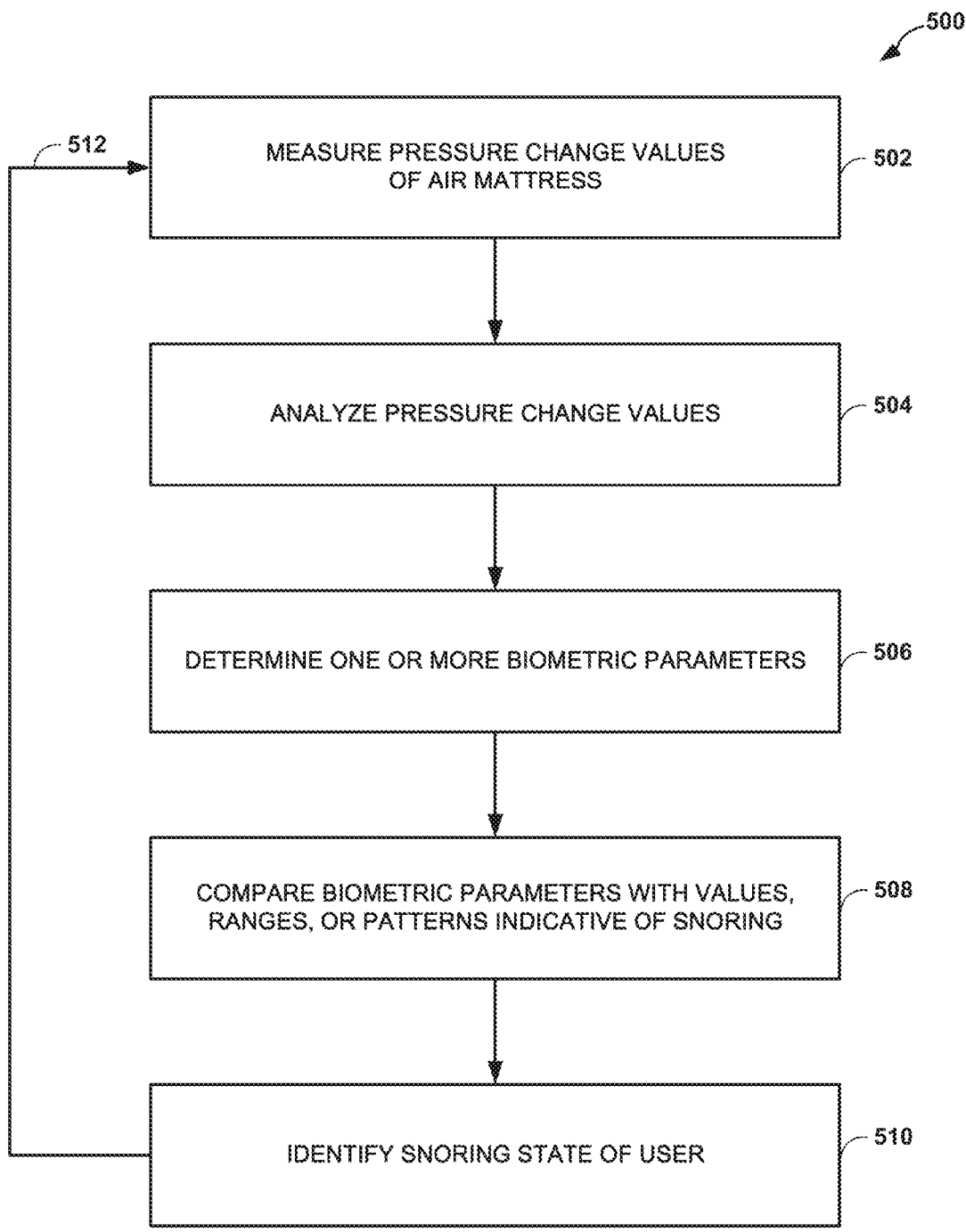
FIG. 5 is a flow diagram depicting an example method of detecting snoring of a user using biometric parameters, in accordance with various techniques of this disclosure.

FIG. 5 is a flow diagram depicting an example method (500) of detecting snoring using biometric parameters. In FIG. 5, the central controller 302 executes instructions that cause a pressure sensing means, such as the pressure transducer 46 of FIG. 2, to measure pressure variations (502). In an example, the pressure can be measured continuously or at a predetermined sample rate. The central controller 302 can analyze the pressure changes detected by the pressure sensing means (504). Using information derived from these analyzed pressure changes, one or more biometric parameters can be determined (506). After determining the one or more biometric parameters of the user, the central controller 302 can compare the biometric parameters with predetermined values, ranges, or patterns which are indicative of snoring (508). In this manner, the central controller 302 can identify snoring by the user (510). After user snoring has been identified, the central controller 302 can continue to monitor the user (512) to determine if the snoring ceases, becomes more severe, becomes less severe, or remains at a substantially constant level.

As previously mentioned, in some example implementations, the techniques for detecting the user's sleep state can be combined with the techniques for detecting snoring using biometric parameters. For example, prior to monitoring pressure changes using the pressure sensing means to determine whether the user is snoring, the central controller 302 can determine whether the user has reached a predetermined sleep state. Thus, determining that the user has reached the predetermined state of sleep can be a prerequisite to instructing the central controller 302 to perform the method 500 described above. Alternatively, the central controller 302 can execute instructions to monitor sleep state and pressure changes simultaneously or substantially simultaneously, and the combined results can be used to determine whether the user is snoring.

In another technique for snoring detection, the system architecture 300 can be configured to detect snoring by monitoring sound waves through a microphone, which can be included in the voice controller 316 as discussed above. In various examples, the system architecture 300 can also be configured to detect snoring by monitoring a combination of both sound waves and biometric parameters. In general, snoring sounds are formed when tissues in the user's throat vibrate as air if flowing through the throat during sleep. In one example implementation, the central controller 302 can execute instructions that cause the voice controller 316 to monitor sound waves generated by the user, and to store the corresponding sound wave signals in a memory device. Processing of the sound wave signals can be performed by the central controller 302, or at a location remote from the bed 301. A snoring state can be determined by monitoring parameters such as the audible level of the sound waves, the frequency of the sound waves, sound wave patterns, and the like. For example, sound waves generated during normal conversation levels of a user may be 40 decibels or less, while sound waves generated by the user's snoring may be in the range of 60-90 decibels or more. By analyzing the sound waves generated by the user, the presence, intensity, duration, and patterns of snoring can be determined.

Figure 6:
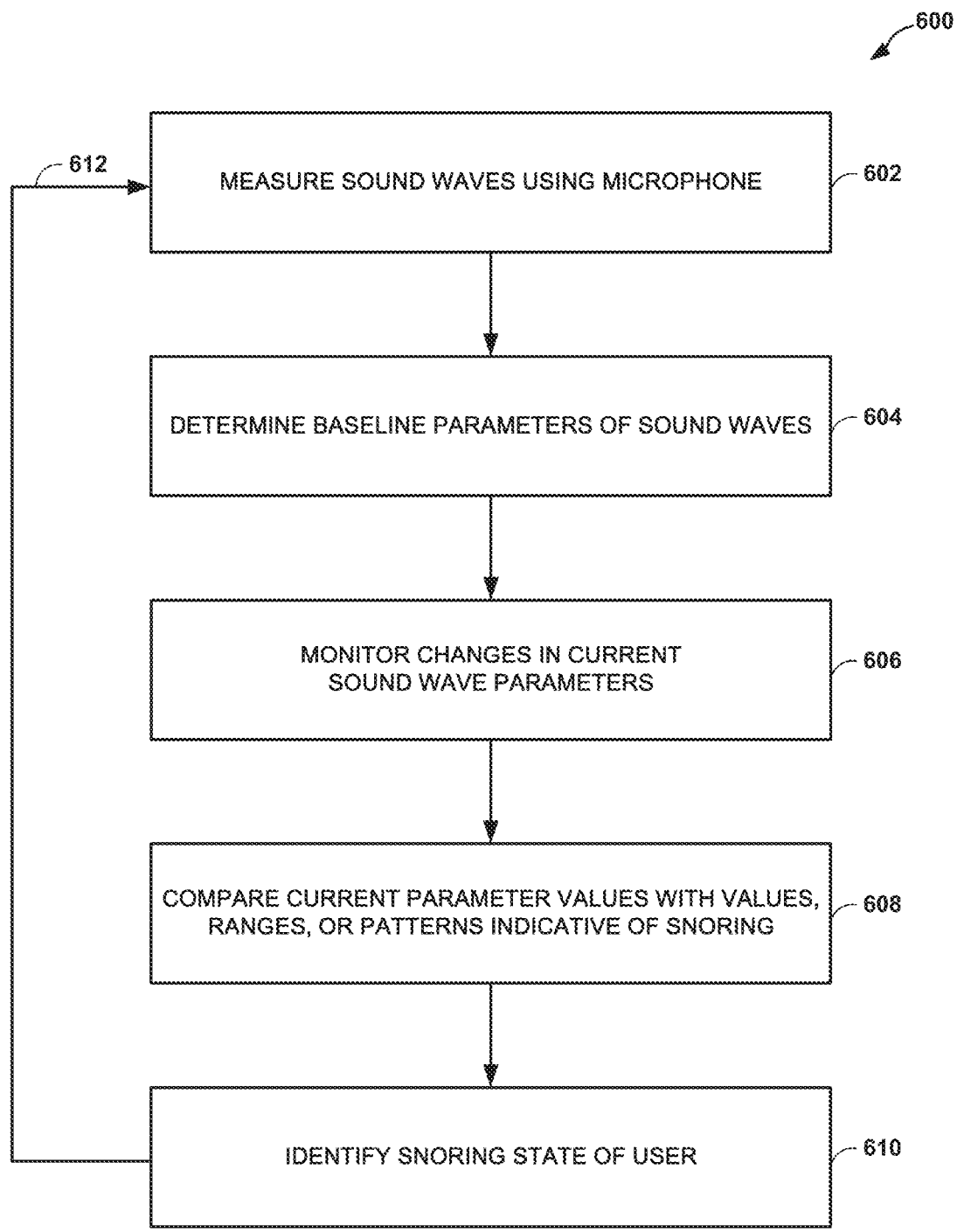
FIG. 6 is a flow diagram depicting an example method of detecting snoring of a user using sound waves, in accordance with various techniques of this disclosure.

FIG. 6 is a flow diagram depicting an example method (600) of detecting snoring using sound waves. In FIG. 6, the central controller 302 executes instructions that cause the voice controller 316 to measure sound waves (602). In an example, the sound waves can be measured continuously or at a predetermined sample rate. The central controller 302 can determine baseline parameters of the sound waves (604) when the user is falling asleep. Then, the central controller 302 can monitor for changes in the current audible level, frequency, and wave patterns (606). If the central controller 302 detects one or more changes with respect to the baseline parameters, the central controller 302 can compare the current parameters with predetermined values or ranges of audible levels and frequencies, as well wave patterns, which are indicative of snoring (608). In this manner, the central controller 302 can identify snoring by the user (610). After user snoring has been identified, the central controller 302 can continue to monitor the user (612) to determine if the snoring ceases, becomes more severe, becomes less severe, or remains at a substantially constant level.

Once again, in some example implementations, the techniques for detecting the user's sleep state can be combined with the techniques for detecting snoring using sound waves. For example, prior to monitoring sound waves using the voice controller 316 to determine whether the user is snoring, the central controller 302 can determine whether the user has reached a predetermined sleep state. Thus, determining that the user has reached the predetermined state of sleep can be a prerequisite to instructing the central controller 302 to perform the method 600 described above. Alternatively, the central controller 302 can execute instructions to monitor sleep state and sound waves simultaneously or substantially simultaneously, and the combined results can be used to determine whether the user is snoring.

Snoring Detection Response Techniques

Figure 7:
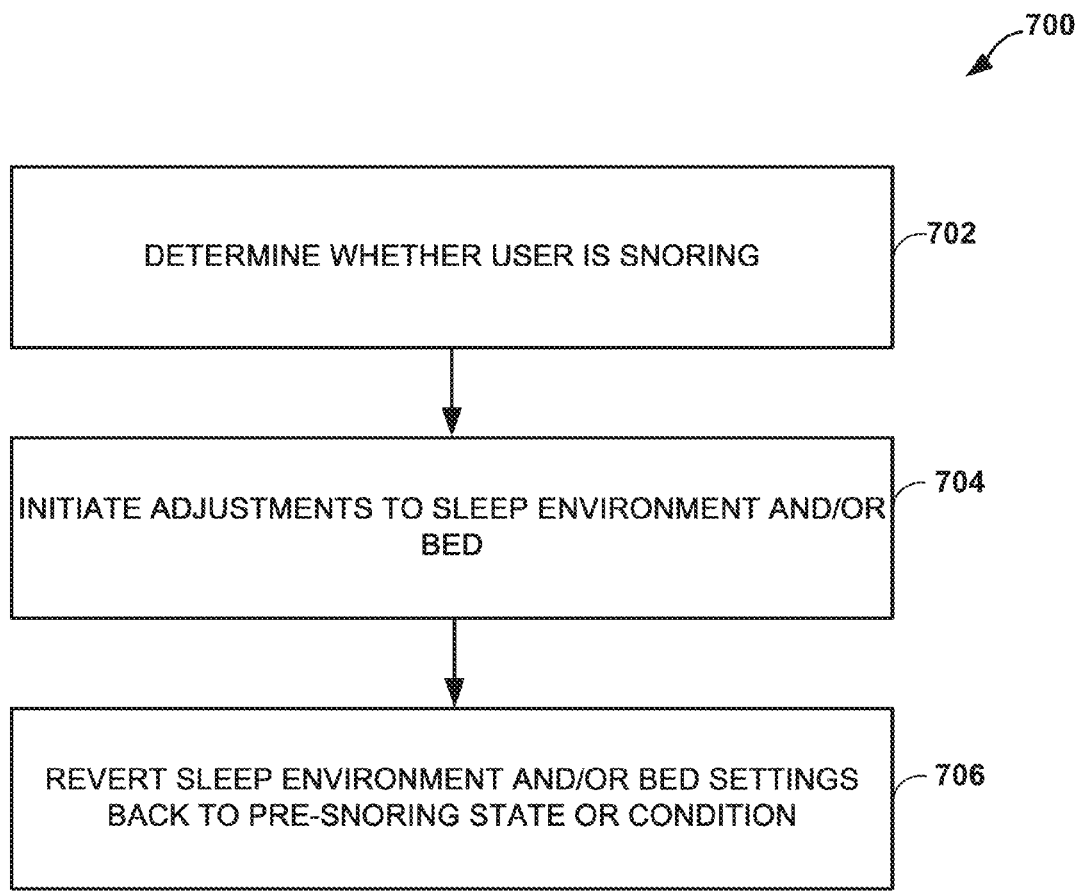
FIG. 7 is a flow diagram depicting an example method of making adjustments to a room environment or a bed in response to detecting snoring of a user, in accordance with various techniques of this disclosure.

FIG. 7 is a flow diagram depicting an example method (700) of initiating one or more adjustments upon detecting that a user is snoring. In FIG. 7, the central controller 302 executes instructions to determine whether the user is snoring (702). Various examples include, but are not limited to, detecting snoring based on analysis of biometric parameters or based on sound waves. When user snoring has been detected, the system architecture 300 and, in particular, the central controller 302, can execute instructions that cause one or more adjustments to the sleep environment and/or the bed 301 to be implemented (704). A non-exhaustive listing and discussion of these various changes is provided below. When the snoring ceases, the central controller 302 can optionally execute instructions that cause one or more of the previous adjustments made to the sleep environment and/or the bed 301 to revert back to the pre-snoring state or condition (706). These optional "re-adjustments" can occur immediately upon detecting that the snoring has ceased, or after a predetermined amount of time has passed since the last snore has been detected.

In an example, the central controller 302 can execute instructions that cause the firmness controller 304 to adjust pressure in the air mattress of the bed 301 when snoring is detected (704). For example, the central controller 302 can provide commands to the firmness controller 304 to increase or decrease pressure in the air mattress, via the pump 305, to a level that can help relieve the snoring. If the system architecture 300 detects that snoring continues even after the pressure in the air mattress has been modified, the central controller 302 can provide additional commands to the firmness controller 304 to further adjust the pressure in the air mattress. Thus, the process of adjusting pressure in the air mattress of the bed 301 to relieve snoring can be iterative. Additionally, if the air mattress includes multiple bladders corresponding to separate zones as discussed above, the central controller 302 can execute instructions that cause the firmness controller 304 to adjust pressure in one or more selected zones, such as the zone corresponding to the head of the user.

In another example, the central controller 302 can execute instructions that cause an adjustment to be made to the foundation 307 when snoring is detected (704). As discussed above, the foundation 307 may include more than one zone, such as a head portion 318 and a foot portion 320, which may be independently adjusted. The user may fall asleep with the foundation 307 in a "flat" position, or with the head portion 318 and/or the foot portion 320 in a raised, articulated position. In various examples, the bed 301 can include a "snore" position defined by a predetermined articulation of the foundation 307. It has been found that, in some cases, snoring can be reduced or prevented by elevating the head of the snoring user by a small amount, which can reduce vibration of the soft tissue in the user's throat. The slight elevation of the snoring user's head can also induce the snorer to change his or her sleeping position, which can cause the snoring to stop. In an example, the snore position can include the head portion 318 being raised at a preset angle θ relative to horizontal. In an example, the angle θ can be from about 5° to about 15° from horizontal, such as about 7°. However, any angle θ that can help reduce or eliminate vibration of soft tissue within the throat of the user can be used. In various examples, the snore position can be customizable to a particular user based on the amount of articulation that is found to help relieve snoring in that user. For example, a large, heavy-set user may require a larger inclination angle than a thin, petite user. Thus, preprogrammed snore positions can be updated in accordance with user preferences and body types.

In another example, the central controller 302 can execute instructions that cause the temperature controller 308 to adjust a temperature of the bed 301 when snoring is detected (704). As discussed above, in various examples, the temperature of the bed 301 (and thus, the user) can be regulated using a pad placed on top of the mattress, a blanket placed on top of the user, or heating/cooling elements incorporated into the mattress, such as a heating/cooling pad integrated into the mattress. Certain users may tend to snore more or less depending on their body temperature and the temperature of the surroundings, such as the bed 301. Thus, heating up or cooling down the bed 301 can help some users find relief from snoring. For example, the temperature of the sleeping surface of the bed 301 could be lowered from 20° Celsius to 18° Celsius when snoring is detected. However, any temperature change, whether positive or negative, can be utilized. Similarly, the central controller 302 can execute instructions that cause the thermostat device 315 to adjust the temperature of the surrounding environment, such as the bedroom where the bed 301 is located, when snoring is detected (704). In view of the foregoing, user temperature can be regulated through use of the temperature controller 308, the thermostat device 315, or both.

The level of light and sound in a bedroom environment can affect the depth and quality of sleep for a user. Thus, when the goal is to alleviate snoring and provide a more restful night of sleep, light and sound can also be controlled to provide an ideal set of sleep conditions. In another example, the central controller 302 can execute instructions for controlling the power status (e.g., on or off) or intensity of light elements 311 or 322A-F placed on and around the bed, and/or for controlling the power status or volume of one or more audio/visual components 313 located near the bed, when snoring is detected (704).

Sleep Profile Reporting

In accordance with the present disclosure, the system architecture 300 can also enable feedback related to snoring to be provided to the user. In various examples, the snoring information processed and analyzed by the central controller 302 can be provided to the user in various formats and to various devices.

In an example, the central controller 302 can execute instructions that cause a sleep profile report to be generated and transmitted to one or more of the remote controller 312, the remote controller 314, or an external computing device such as, for example, a personal computer (PC), a tablet PC, a Personal Digital Assistant (PDA), or the like. The external computing device can be operably coupled to the bed 301 via any suitable network connection, including those previously described.

Figure 8:
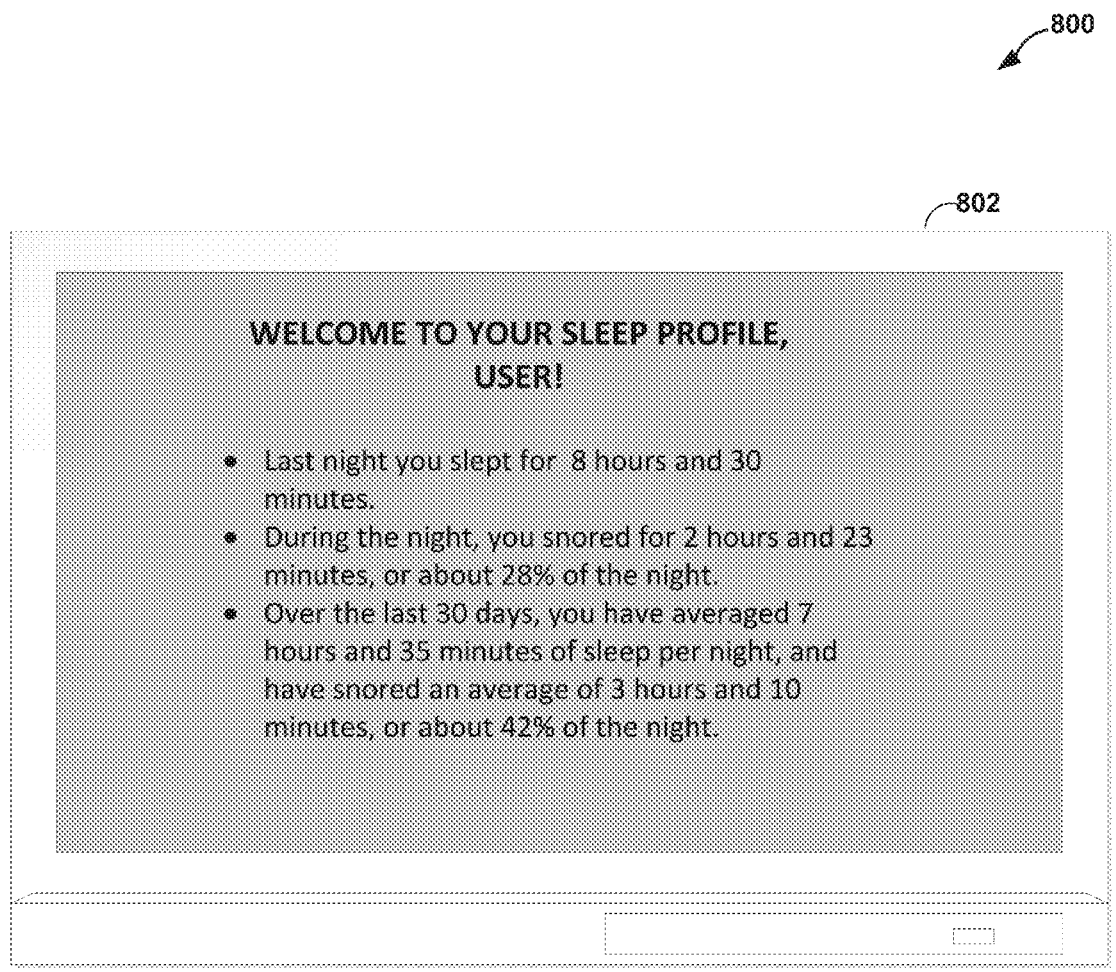
FIG. 8 is a diagrammatic representation of a sleep profile report generated on a laptop computer, in accordance with various techniques of this disclosure.

FIG. 8 is a diagram illustrating a sleep profile report 800 generated on a laptop computer 802. In an example, the sleep profile report 800 can indicate the total amount of time that the user was asleep during the night (or day). The sleep profile report 800 can also indicate the times at which the user fell asleep and woke up. The total amount of time that the user was asleep can be determined using any suitable technique, including monitoring pressure changes in an air mattress as discussed above and deriving the sleep time from information related to the user's state of sleep throughout the night. As further shown in FIG. 8, the sleep profile report 800 can quantify the amount of time that the user was found to be snoring while asleep during the night. In various examples, the snoring duration can be presented as a total number of hours and minutes, as a percentage, or both.

Sleep profile reports 800 can be stored in memory associated with the system architecture 300 for recall at a later time. In an example, the central controller 302 can execute instructions that cause the sleep profile report 800 to display the amount of sleep that a user has averaged over a specified number of days, and the amount of snoring that the user has averaged during that time. For example, the sleep profile report 800 shows average sleep and snoring over the previous 30 days. However, a number of days greater than or less than 30 can also be used.

Although various embodiments have been described with reference to specific example embodiments, it will be evident that various modifications and changes may be made to these embodiments without departing from the broader spirit and scope of the invention. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled. As is common, the terms "a" and "an" may refer to one or more unless otherwise indicated.

The invention claimed is:

1. A bed system comprising:
an inflatable air mattress;
an adjustable foundation;
a pressure sensor for sensing pressure of the air mattress;
a pump; and
a central controller comprising:
a processor configured to:
analyze pressure signals obtained from the pressure sensor to determine one or more biometric parameters for a user on the air mattress;
compare the one or more biometric parameters with predetermined values, the predetermined values being indicative of snoring;
determine whether the user on the air mattress is snoring based on comparing the one or more biometric parameters with the predetermined values; and
transmit, in response to determining that the user is snoring, at least one instruction to adjust a head position of the adjustable foundation.

2. A method comprising:
determining, at the central controller of the bed system of claim 1, whether the user is snoring; and
in response to determining that the user is snoring, adjusting a head position of the adjustable foundation of the bed system.

3. The method of claim 2, wherein the bed system includes the inflatable air mattress supported by the adjustable foundation.

4. The method of claim 3, further comprising adjusting a pressure of the inflatable air mattress, in response to determining that the user is snoring.

5. The method of claim 2, wherein determining whether a user is snoring comprises measuring sound waves using a sound measuring device.

6. The bed system of claim 1, wherein the processor is configured to adjust a pressure of the air mattress, in response to determining that the user is snoring.

7. The bed system of claim 1, wherein the processor is configured to determine whether a user on the air mattress is snoring based on sound waves generated by the user.

8. The bed system of claim 1, wherein the pump is operably connected to the inflatable air mattress and the pressure sensor comprises a pressure transducer positioned in the pump and fluidically connected to both a manifold of the pump and to the inflatable air mattress.

9. The bed system of claim 1, further comprising:
a first air chamber; a first pressure sensor for sensing air pressure of the first air chamber a second air chamber; and a second pressure sensor for sensing air pressure of the second air chamber
wherein the processor is further configured to:
detect biometric parameters for a first user supported by the first air chamber;
detect biometric parameters for a second user supported by the second air chamber;
determine, based on the biometric parameters detected for the first and second users, that one of the first and second users is snoring;
transmit, in response to determining that one of the first and second users is snoring, at least one instruction to adjust a head position of a portion of the adjustable foundation supporting one of the first or second air chambers based on determining which of the first and second users is snoring.

10. The bed system of claim 1, wherein comparing the one or more biometric parameters with the predetermined values indicative of snoring is performed in response to determining that the user has reached a predetermined sleep state.

11. A bed system comprising:
an inflatable air mattress;
an adjustable foundation;
a pressure sensor for sensing pressure of the air mattress; and
a central controller comprising:
a pump; and
a processor configured to:
determine whether a user on the air mattress is snoring based on pressure signals obtained from the pressure sensor;
transmit, in response to determining that the user is snoring, at least one instruction to adjust a head position of the adjustable foundation;
transmit, in response to determining that the user is snoring, at least one instruction to adjust a pressure in the inflatable air mattress;
transmit, in response to determining that the user is snoring, at least one instruction to adjust a temperature;
transmit, in response to determining that the user is snoring, at least one instruction to adjust a light;
transmit, in response to determining that the user is snoring, at least one instruction to adjust a sound volume; and
transmit, in response to determining that the user is snoring, at least one instruction to adjust a vibration.

* * * * *